United States Patent [19]

Abu-Shumays

[11] 4,180,739
[45] Dec. 25, 1979

[54] THERMOSTATABLE FLOW CELL FOR FLUORESCENCE MEASUREMENTS

[75] Inventor: Ahmad Abu-Shumays, Los Altos, Calif.

[73] Assignee: Varian Associates, Inc., Palo Alto, Calif.

[21] Appl. No.: 864,137

[22] Filed: Dec. 23, 1977

[51] Int. Cl.² .............................................. G01N 21/38
[52] U.S. Cl. .................................. 250/461 R; 250/458
[58] Field of Search ............... 250/458, 459, 461, 373, 250/432, 434, 484, 485; 356/51, 85, 244, 246

[56] References Cited
U.S. PATENT DOCUMENTS

| | | | |
|---|---|---|---|
| 3,151,204 | 9/1964 | Stacy | 250/461 R |
| 3,869,215 | 3/1975 | Nolan | 356/246 |
| 4,008,397 | 2/1977 | Zdrodowski | 250/461 R |
| 4,082,459 | 4/1978 | Wolfe | 250/458 |

*Primary Examiner*—Bruce C. Anderson
*Attorney, Agent, or Firm*—Stanley Z. Cole; John J. Morrissey; Gerald M. Fisher

[57] ABSTRACT

This thermostatable flow cell for fluorescence measurements enables rapid thermal equilibration and precise temperature control. For a flow cell volume of less than 20 microliters, a selected temperature in the range up to 20° C. above ambient can be attained within five seconds, and this selected temperature can be maintained stable within 0.1° C. The cell comprises a cylindrical cavity whose walls include a metallic portion for heat conduction and a transparent window portion for light acceptance and fluorescence observation. The metallic portion of the cell is formed from a cell block to which a temperature sensing means is affixed. The window portion is affixed to the cell block by an inert bonding material. A thermoelectric device responsive to the temperature sensing means causing heating or cooling of the cell block as necessary to provide thermal equilibration at the selected temperature.

12 Claims, 5 Drawing Figures

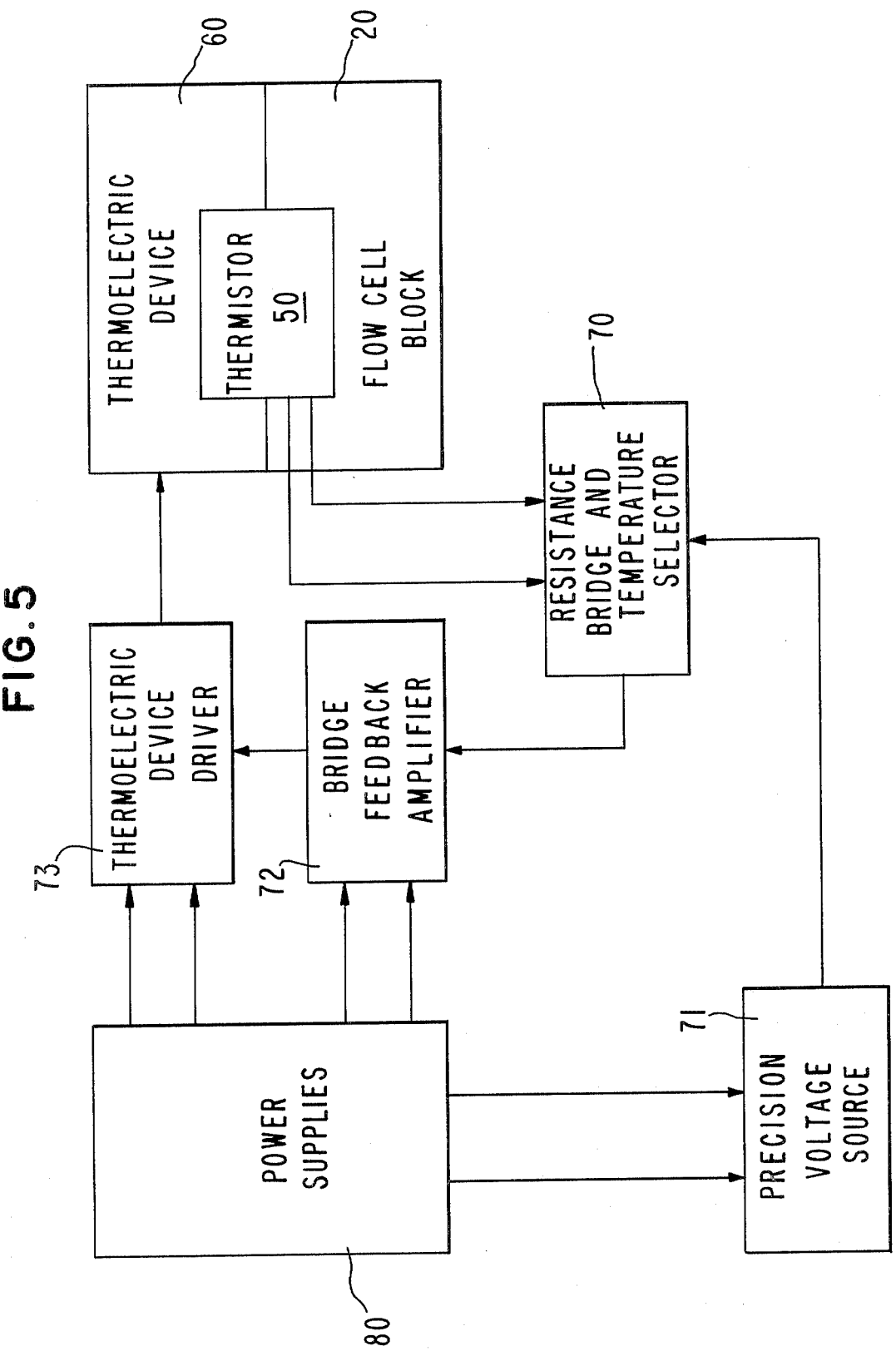

THERMOSTATABLE FLOW CELL FOR FLUORESCENCE MEASUREMENTS

BACKGROUND OF THE INVENTION

In a flow cell for use in making fluorescence measurements, a window must be provided of sufficient size to permit entry into the cell of exciting radiation through a large solid angle (called the "acceptance" angle), and to permit observation of the resulting fluorescence emissions along a line at a large angle (typically 90°) from the path of the exciting radiation. Thermostatted flow cells for fluorescence measurements have been used in the past in applications where precise temperature control is important. Thus, in the prior art, instruments were known in which a constant-temperature fluid could be circulated through a jacket surrounding the flow cell. Also, thermoelectric devices using the Peltier effect were known to the prior art as temperature controllers.

With such thermostatted flow cells known to the prior art, however, the large mass of the circulating fluid jackets prevented rapid temperature equilibration. Even with devices using thermoelectric temperature controllers, relatively large masses were required for the components in which the thermoelectric devices were embedded, and consequently rapid temperature equilibration could not be provided.

For typical thermostatted flow cells known to the prior art, the time required for liquid in the flow cell to reach 37° C. from ambient room temperature was on the order of 15 seconds or longer. Furthermore, there were no thermostatted microflow cells (i.e., flow cells having a volume of less than 20 microliters) available for use in making fluorescence measurements.

SUMMARY OF THE INVENTION

It is an object of the present invention to provide a thermostatted flow cell for use in making fluorescence measurements.

It is a particular object of this invention to provide a thermostatted flow cell for use in making fluorescence measurements, which flow cell provides rapid temperature equilibration (i.e., on the order of five seconds) and precise temperature control (i.e., within a temperature variation of 0.1° C.).

It is more particularly an object of this invention to provide a thermostatted microflow cell for use in making fluorescence measurements.

It is a further object of this invention to provide a thermostatted mircoflow cell for use in making fluorescence measurements, which cell provides rapid temperature equilibration and precise temperature control, and also is easily flushable by the fluid passing therethrough so as to preclude the entrapment of contaminants within the cell.

It is also an object of this invention to provide a thermostatted microflow cell for use in making fluorescence measurements, which cell has minimal mass to facilitate rapid changes in operating temperature.

It is a further object of this invention to provide a thermostatted microflow cell for use in making fluorescence measurements, which cell has a transparent window portion of sufficient size to enable a large exciting radiation flux to enter the cell and to permit observation of resulting fluorescence emissions at a large viewing angle (typically at a 90° angle) from the path of the exciting radiation.

It is another object of this invention to provide a thermostatted microflow cell for use in making fluorescence measurements wherein a temperature sensing means is disposed in close proximity to the flow channel through the cell, and wherein a thermoelectric device is disposed in close proximity to the temperature sensing means, whereby rapid response of the thermoelectric device to changes in the temperature of fluid flowing through the flow channel can be effected.

It is a particular object of this invention to provide a thermostatted microflow cell for use in fluorescence spectroscopy, which cell has a cylindrical flow channel that eliminates unpurgeable "dead" volumes within the flow cell.

Another object of this invention is to provide a thermostatted microflow cell that is formed from a block of metallic material to which a transparent window structure, typically made from fused quartz, is affixed by an inert bonding material.

A more particular object of this invention is to provide a thermostatted microflow cell in which the flow channel is formed from a hemi-cylindrical quartz section that provides a large acceptance angle for admitting exciting radiation and for viewing fluorescence emissions, and a hemicylindrical metallic section that provides a heat-conducting path for the maintenance of a constant temperature in the flow channel.

DESCRIPTION OF THE DRAWING

FIG. 5 shows a block diagram for an electrical circuit to operate a thermostatted flow cell according to this invention.

DESCRIPTION OF PREFERRED EMBODIMENT

Figure 1:
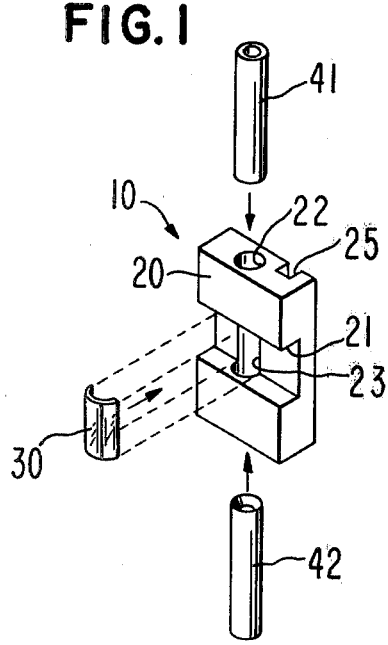
FIG. 1 is an exploded view of a thermostatted flow cell according to this invention, showing the metallic cell block, the transparent window portion, and associated inlet and outlet tubing.

FIG. 1 shows an exploded view of a thermostatable flow cell 10 according to this invention. Preferably, this is a microflow cell, i.e., a cell whose flow volume is less than 20 microliters. The flow cell 10 is fabricated from a metallic block 20, which may be of any metal that is substantially chemically inert with respect to the fluid flowing through the flow cell. Cells constructed of stainless steel, copper and brass have been evaluated, and have been found to give substantially identical results in terms of thermal equilibration and temperature control, which are the prime considerations influencing the design of a flow cell according to this invention. Stainless steel has been found to be a suitable material for most fluids of interest.

As seen in FIG. 1, the metallic block 20 has a generally rectangular or square configuration on its broad faces (typical dimensions being 1 cm by 2 cm), and a thickness of about 0.3 cm. The flow channel is formed by removing a rectangular slot or notch portion 21 from the central region on one of the broad faces to a depth of about half the thickness of the block 20, and by drilling a cylindrical bore 22 of about 0.2 cm diameter through the narrow faces of the block 20 along an axis transverse to the axis of the slot 21. The bore 22 assumes the configuration of a hemi-cylindrical groove 23 in the region of the slot 21. A transparent hemi-cylindrical window 30, preferably made of fused quartz, is placed in the slot 21 to cover the hemi-cylindrical groove 23. The surface of the groove 23 is preferably polished to reflect incident radiation that enters the flow cell 10 through the window 30 back into the interior of the flow cell so as to concentrate the radiation flux available for causing fluorescence emissions. The quartz window 30 is bonded to the metallic block 20 by any suitable technique known to the prior art, such as an inert ceramic or a silicon-rubber bonding material.

The dimensions suggested herein for the block 20, and for the flow channel formed thereby in conjunction with the quartz window 30, are not critical but rather are convenient in order to accomplish rapid thermal equilibration and precise temperature control within the flow channel. The thermal conductivity of the fluid passing through the flow channel will, in general, be two to three orders of magnitude lower than the thermal conductivity of most metals. Thus, the rapidity of thermal equilibration within the flow channel can be minimized by minimizing the volume of the flow channel. For this reason, a microflow cell is preferred in applications where rapidity of thermal equilibration is important, e.g., in clinical applications involving temperature-dependent chemical reactions, and in applications requiring rapid throughput for performing measurements on a large number of samples.

The flow cell internal volume is preferably of cylindrical configuration so as to provide a minimum volume, which has a hydrodynamic geometry that is most suitable for liquid flow applications—i.e., an internal configuration that is without recesses (or "dead volumes") in which contaminants might become trapped. Inlet and outlet tubing members 41 and 42, which may advantageously be made of stainless steel, are pressed into the bore 22 of the metallic block 20 on respective sides of the slot 21. The outer diamter of the tubing members 41 and 42 substantially coincides with the diameter of the bore 22 to provide a fluid-tight fit. At the respective ends of the bore 22, the tubing members 41 and 42, respectively, can be sealed to the metallic block 20 by any suitable technique such as soldering or welding.

A cavity 25 is provided on the rear face of the block 20, i.e., behind the face on which the window 30 is disposed. A means for sensing the temperature of the block 20, and consequently the temperature within the flow cell 10, can be disposed within this cavity 25.

Figure 2:
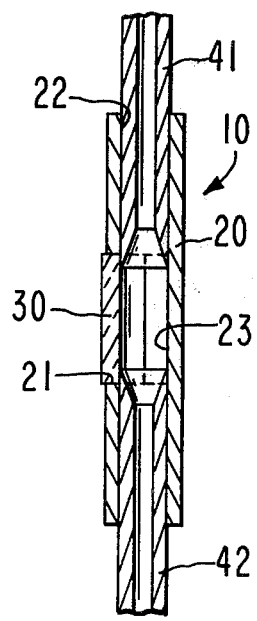
FIG. 2 is a cross-sectional view of the assembled flow cell that is shown in exploded view in FIG. 1. The cross-sectional view of FIG. 2 is longitudinal with respect to the axis of the flow cell.

FIG. 2 shows a cross-sectional view of an assembled flow cell that was shown in exploded view of FIG. 1. The inlet and outlet tubing members 41 and 42 are shown inserted into respective ends of the bore 22 of the block 20. The ends of the tubing members 41 and 42 extend through the respective ends of the bore 22 into respective ends of the flow cell 10, whose flow channel is defined by the transparent window 30 and the groove 23 in the slot 21. In this way, the ends of the tubing members 41 and 42 provide support for the axial ends of the transparent window 30.

The inner bores of the tubing members 41 and 42 are flared conically outward in the vicinity of their respective interfaces with the flow cell 10 in order to match the diameter of the interior of the flow cell 10. In this way, fluid passing through the flow cell 10 does not experience any sharp diametric discontinuities at the ends of the tubing members 41 and 42. Thus, hydrodynamic effects that would occur if such discontinuities were present are eliminated. Furthermore, the smoothly continuous flow path through the flow cell 10 via the tubing members 41 and 42 eliminates any pockets or "dead volumes" in which quantities of fluid can become trapped. The flow cell 10 is continuously swept or flushed by the fluid passing therethrough, whereby the accumulation of contaminants within the flow cell 10 is prevented.

The metallic block 20 provides a heat transfer path for heating or cooling the flow channel as necessary in order to maintain the fluid flowing therethrough at a constant desired temperature. In order to facilitate rapid changes of operating temperature, the mass of the metallic block 20 is kept as small as possible consistent with the structural requirement that the block 20 be rigid and be large enough to couple the inlet and outlet tubing members 41 and 42, respectively, to the bore 22.

Figure 3:
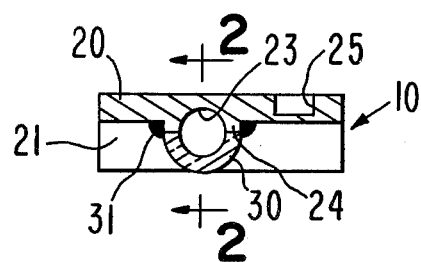
FIG. 3 is a different cross-sectional view of the assembled flow cell that is shown in exploded view in FIG. 1. The cross-sectional view of FIG. 3 is transverse with respect to the axis of the flow cell.

FIG. 3 shows a transverse cross-sectional view of the assembled flow cell that was shown in longitudinal cross section in FIG. 2. The hemi-cylindrical transparent window 30 is shown bonded to the metallic body 20 by a bonding material 31, which may be of ceramic or silicon rubber. In the embodiment shown in FIG. 3, the slot 21 is cut to a depth slightly greater than half the thickness of the block 20, so as to provide lip portions 24 along either side of the hemi-cylindrical groove 23. The bonding material 31 effectively seals the edges of the hemi-cylindrical window 30 to the lip portions 24 along the groove 23.

Figure 4:
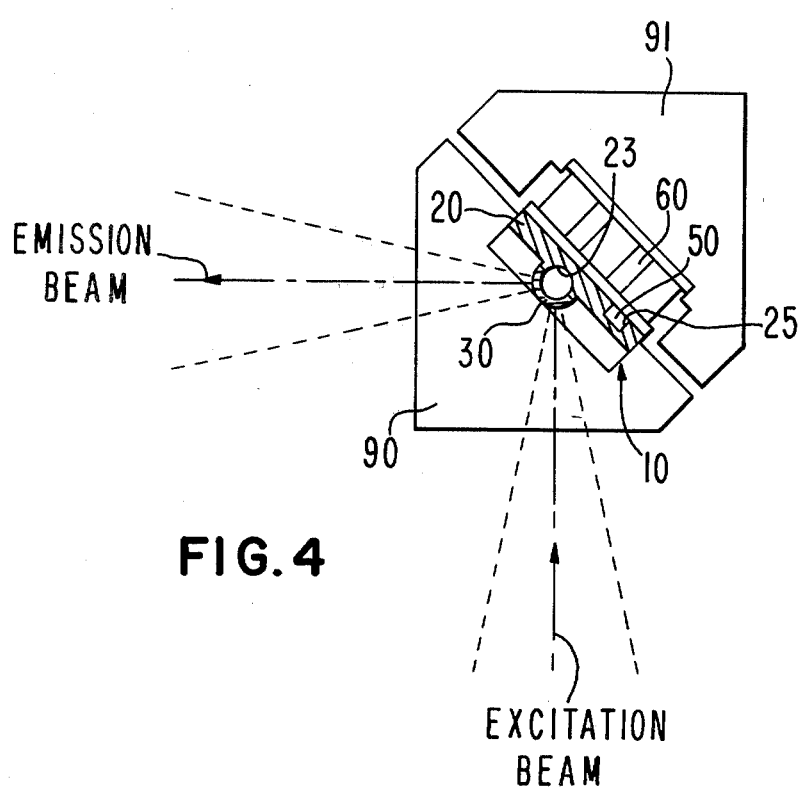
FIG. 4 is a cross-sectional view of a flow cell assembly according to this invention showing a temperature sensing means affixed to the metallic cell block, and an adjacent thermoelectric device responsive to the temperature sensing means for regulating the temperature in the flow cell.

In FIG. 4, the flow cell 10 is shown in an assembly that also comprises a temperature sensing means 50, which may be a thermistor, embedded in a thermally conducting compound disposed in the cavity 25. Also shown in FIG. 4 as part of the overall flow cell assembly is a thermoelectric device 60, which is operable by means of an electrical circuit in response to temperature changes in the flow cell 10 so as to cause heating or cooling of the flow cell 10 as necessary to maintain a constant desired temperature therein. Also depicted in FIG. 4 are an insulating cover 90 that isolates the flow cell 10 from the ambient environment, and a metallic support structure 91 that functions as a heat sink.

FIG. 5 shows in block diagram a suitable electrical circuit for thermostatically controlling the temperature within the flow cell 10. The temperature sensing means 50, which is preferably a thermistor affixed in thermally conductive contact to the metallic block 20, is an element of a bridge network 70 in a null detection circuit. Another element of the bridge network 70 is a variable resistor, whose selected value of resistance determines the desired equilibration temperature for the flow cell 10. A precision voltage source 71 energizes the bridge network 70, which preferably comprises means for selecting a number of "set" temperatures. Typically, four "set" temperatures would be sufficient. When the thermistor 50 senses the selected equilibration temperature, the bridge network 70 is balanced and yields a null output signal. Any deviation of the sensed temperature of the flow cell 10 from the selected equilibration temperature causes a positive or negative output signal to be generated by the bridge network 70. The magnitude and sign of this output signal is sensed by a differential feedback amplifier 72, which generates a signal to cause a driving means 73 to drive the thermoelectric device 60 so as to heat or cool the block 20, as appropriate, until the bridge network 70 is balanced (i.e., has a null output), whereupon the selected equilibration temperature is reestablished.

Power supplies, indicated generally by the reference number 80, supply power to the variable voltage source 71, the differential feedback amplifier 72 and the thermoelectric device driving means 73. Double lines are shown from the power supplies 80 to the voltage source 71, the amplifier 72 and the driving means 73 in order to indicate the possibility of providing signals for causing the driving means 73 either to heat or to cool the thermoelectric device 60. The power dissipated in the thermoelectric device 60 is proportional to the deviation of the sensed temperature in the flow cell 10 from the selected equilibration temperature.

This invention has been described with reference to preferred embodiment, but variations with respect to geometrical configurations and dimensions can readily be adopted by those skilled in the art. Accordingly, the foregoing disclosure is to be construed as illustrative rather than as limiting. The scope of the invention is defined by the following claims.

What is claimed is:

1. A flow cell assembly for fluorescence measurements, including means for obtaining temperature equilibration of a liquid sample in less than 15 seconds, including cavity forming means having a volume less than 20 microliters for containing a fluid sample to be analyzed, said cavity forming means comprising a first wall portion that is metallic and a second wall portion that is transparent to electromagnetic radiation, said first wall portion comprising a surface region on a metallic block, said second wall portion being affixed to said metallic block, said second wall portion being of a size sufficient to enable entry of a flux of exciting radiation into said cavity and observation of fluorescence emissions caused in said fluid sample by said exciting radiation;
   a temperature sensing means affixed to said metallic block; and
   means responsive to said temperature sensing means for driving a thermoelectric device so as to maintain, in operation, the temperature of said sample within said cavity at a desired value.

2. The flow cell assembly of claim 1 further comprising inlet and outlet means for the flow of said sample fluid through said cavity.

3. The flow cell assembly of claim 1 wherein said first and second wall portions are configured to provide a generally cylindrical cavity.

4. The flow cell assembly of claim 3 wherein said first and second wall portions are each of hemicylindrical configuration.

5. The flow cell assesmbly of claim 2 wherein said inlet and outlet means comprise tubing structures, the bores of said tubing structures being flared conically outward at the interfaces of said tubing structures with said cavity.

6. The flow cell assembly of claim 1 wherein said metallic block is made from stainless steel.

7. The flow cell assembly of claim 1 wherein said surface region on said metallic block is a reflective cylindrical surface.

8. A fluorescence cell comprising,
   means for equilibrating, in operation, the temperature of a portion of a liquid sample within 0.1 degrees centigrade of a predetermined temperature in a range up to 20 degrees centigrade from ambient temperature in less than 15 seconds, said means including sample contacting surfaces of said cell, said sample contacting surfaces of said cell for containing said portion of said liquid sample being configured to contain less than 20 microliters, said sample contacting surfaces being further configured such that a first substantial portion of said sample contacting surfaces are metallic,
   a thermoelectric heating and cooling means, said thermoelectric means being mounted directly and intimately to the back side of said metallic portion of said sample contacting surfaces in close proximity to said liquid sample, and
   radiation transmissive means for transmitting light to excite, in operation, said portion of liquid sample and for permitting non-colinear observation of fluorescence radiation emitted from said sample, said transmissive means being substantially all the remaining portion of said sample contacting surfaces.

9. The flow cell of claim 8 wherein said remaining portion of said sample containing surfaces of said cell permits observation of said fluorescence along a line 90 degrees displaced from the axis of said light for exciting.

10. The cell of claim 9 wherein said remaining portion of said sample contacting surfaces is of hemicylindrical shape and is fixedly attached to said first substantial portion of said sample containing surfaces.

11. The cell of claim 10 wherein said first portion of said sample containing surfaces is of hemicylindrical shape and is provided with a highly optically reflective surface to optical wavelengths.

12. The cell of claim 10 wherein said first portion of said sample contacting surfaces is a hemicylindrical groove in a metallic block and wherein a temperature sensing device is disposed in a depression in said metal block to provide a highly intimate thermal contact with said portion of said liquid sample.

* * * * *